United States Patent
Angelosante et al.

(10) Patent No.: US 10,359,360 B2
(45) Date of Patent: Jul. 23, 2019

(54) OPTIMAL WEIGHTED AVERAGING PRE-PROCESSING SCHEMES FOR LASER ABSORPTION SPECTROSCOPY

(71) Applicant: ABB, Inc., Cary, NC (US)

(72) Inventors: Daniele Angelosante, Turgi (CH); Andrew Fahrland, Sunnyvale, CA (US); Deran Maas, Zurich (CH); Manish Gupta, Mountain View, CA (US)

( * ) Notice: Subject to any disclaimer, the term of this patent is extended or adjusted under 35 U.S.C. 154(b) by 220 days.

(21) Appl. No.: 15/005,384

(22) Filed: Jan. 25, 2016

(65) Prior Publication Data
US 2017/0212042 A1    Jul. 27, 2017

(51) Int. Cl.
| | | |
|---|---|---|
| G01N 21/39 | (2006.01) | |
| G01J 3/02 | (2006.01) | |
| G01J 3/42 | (2006.01) | |
| G01J 3/28 | (2006.01) | |
| G01J 3/433 | (2006.01) | |

(52) U.S. Cl.
CPC .............. G01N 21/39 (2013.01); G01J 3/027 (2013.01); G01J 3/28 (2013.01); G01J 3/42 (2013.01); G01J 3/433 (2013.01); *G01J 2003/2853* (2013.01); *G01N 2021/399* (2013.01); *G01N 2201/12* (2013.01)

(58) Field of Classification Search
CPC combination set(s) only.
See application file for complete search history.

(56) References Cited

U.S. PATENT DOCUMENTS

| | | | |
|---|---|---|---|
| 6,940,599 B1 | 9/2005 | Hovde | |
| 8,711,357 B2 | 4/2014 | Liu et al. | |
| 2005/0188859 A1* | 9/2005 | Bruce, III | G01N 21/359 |
| | | | 99/486 |
| 2015/0138538 A1* | 5/2015 | Sakurai | G01J 3/0291 |
| | | | 356/72 |
| 2016/0195508 A1* | 7/2016 | Al-Hajji | G01N 33/2823 |
| | | | 250/301 |
| 2017/0059477 A1* | 3/2017 | Feitisch | G01N 21/274 |

OTHER PUBLICATIONS

P.W. Werle et al., "Signal Processing and Calibration Procedures for in Situ diode-laser Absorption Spectroscopy", Science Direct, Spectrochimica Acta Part A 60, 2004, pp. 1685-1705.

* cited by examiner

*Primary Examiner* — Mamadou L Diallo
(74) *Attorney, Agent, or Firm* — Barnes & Thornburg LLP (57) ABSTRACT

A method of processing raw measurement data from a tunable diode laser absorption spectroscopy (TDLAS) tool or other spectroscopic instrument is provided that determines what types of noise (electronic or process flow) are present in the measurement. Based on that determination, the noise is reduced by performing a weighted averaging using weights selected according to the dominant type of noise present, or a general case is applied to determine weights where neither noise type is dominant. The method also involves performing continuous spectroscopy measurements with the tool, with the data and weighted averaging being constantly updated. Weighting coefficients may also be adjusted based on similarity or difference between time-adjacent traces.

17 Claims, 6 Drawing Sheets

OPTIMAL WEIGHTED AVERAGING PRE-PROCESSING SCHEMES FOR LASER ABSORPTION SPECTROSCOPY

TECHNICAL FIELD

The present invention relates to spectroscopic measurement and more particularly to pre-processing of raw data from such measurement to reduce noise and remove unwanted artifacts from the raw data.

BACKGROUND ART

One of the problems occurring in spectrometry is noise that arises from electronic sensor fluctuations, illumination fluctuations, as well as time-varying transmission due to process flow variations, density gradients, dust, and the like. Conventional tunable diode laser absorption spectroscopy (TDLAS) systems and many other spectroscopic measurement systems often experience degradation in performance due to various noise sources.

A typical prior art spectrometry measurement is described, for example, in U.S. Pat. No. 8,711,357 to Liu et al, which provides for a reference and test harmonic absorption curves from a laser absorption spectrometer having a tunable or scannable laser light source and a detector. The absorption curves are generated by the detector in response to light passing from the laser light source through respective reference and sample gas mixtures. The reference curve might be determined for the spectrometer in a known or calibrated state. The shape of the test harmonic absorption curve is compared with that of the reference harmonic absorption curve and parameters of the laser absorption spectrometer are adjusted to reduce the difference and correct the test curve shape.

U.S. Pat. No. 6,940,599 to Hovde describes, spectral demodulation in absorption spectrometry, wherein the spectral response of a detector can be characterized in Fourier space.

However, neither of these methods deals directly with the presence of noise in the absorption signal. They would each perform better if the noise could first be reduced or removed from the signal obtained from the detector.

Typically, conventional spectroscopic signal analysis will pre-process the signal using simple averaging of successive measurements or traces obtained \ from multiple scans of the laser wavelengths. It does not use any weighted average or determine any optimal weighting scheme based on realistic noise models. As such, while this simple averaging may be adequate in r laboratory or ideally-controlled conditions, in more harsh or uncontrolled measurement environments it may suffer unacceptable degradation of performance due to an inability to reduce the noise in the signal sufficiently. Beyond a certain limit, the systems can no longer operate and report data reliably due to insufficient noise suppression. This is a recurring problem for any field-deployed TDLAS systems or any spectroscopic system used in an environment where harsh real-world conditions such as dust, density gradients, temperature gradients, and mechanical movement can lead to noise.

It is desired, to provide processing schemes that can suppress noise so as to improve overall sensor performance and extend the range of conditions under—which spectroscopic systems can reliably operate. Noise levels from a variety of sources due to electronics, laser fluctuation, or time-varying transmission through the process flow should be able to be successfully reduced.

SUMMARY DISCLOSURE

A signal processing scheme uses a realistic noise model to assess a tunable diode laser absorption spectroscopy (TDLAS) or other spectroscopic measurement signal when that signal undergoes amplitude variations from the various noise sources from (a) laser intensity fluctuations, (b) process flow variations (e.g., dust, density gradients and other time-varying transmission losses), and (c) electronic and detection system noise. An optimal averaging strategy depends upon the type of noise expected and found by the analyzer system. The noise model accounts for the presence of any or all of these potential noise sources to select a weighted averaging scheme that is optimized according to which, if any, of the noise sources happens to be dominant under the prevailing measurement conditions.

The method of processing spectroscopic raw data, such as tunable diode laser absorption spectroscopy (TDLAS) measurement signals, begins by obtaining the raw data, e.g. by measuring the amplitude of each laser scan. Then, optimal weighting coefficients are chosen based on whether the noise is dominated by electronic sources independent of the measured volume, or the noise is dominated by changes in the measurement volume, or a general case where neither noise source dominates the other. If detector noise is negligible and process flow fluctuations dominate, the received signal should be normalized by amplitude. On the other hand, if detector noise dominates, the received signal should be— multiplied by the amplitude. If both effects contribute significantly, a generic formula can set the appropriate weights. After completing a weighted average calculation using the determined optimal weighting coefficients, the resulting spectrum is analyzed to produce the desired measured quantity.

The measurement noise to be reduced by the appropriate choice of weighting coefficients may be caused by any one or more of electrical sources, process flow variations, attenuation due to dust or particulates, density gradients in the flow, or other time-varying transmission losses. Measurement of the amplitude of each laser scan may be determined by any of peak-to-peak signal amplitude, signal amplitude at a specific measurement point or during a specific duration of time during the TDLAS trace, signal amplitude with a background signal subtracted, or slope of the ramp portion of the TDLAS trace.

Weighting factors may also be adjusted based upon similarity to time-adjacent traces either prior or post to the current measurement trace. To make such adjustments, the system can calculate the differences between the current trace and the prior (and/or post) trace, squaring those differences between the two traces, calculating an additional weighting factor by summing and taking the inverse of the sum, then additional weighting factor by the original weighting factor.

Advantages of this pre-processing scheme include (a) improved sensor performance; (b) reduction in noise of measured values reported by the spectroscopy instrument; and (c) resistance to laser power fluctuations, dust, beam steering, density gradients, temperature gradients, and mechanical movement in the process that would otherwise lead to degradation of sensor performance. The weighted average, calculated based on the noise model parameters and parameters of the measured signal, reduces noise below that which is achievable by the traditional equal-weighted simple averaging scheme. In this way, performance (i.e. precision and accuracy) of TDLAS and other spectroscopic instruments is enhanced so that such instruments can be deployed even in harsh environments so as to successfully measure data near its limits of detectability.

DETAILED DESCRIPTION

A data averaging scheme is presented to optimally process raw spectroscopy data, such as a tunable diode laser absorption spectroscopy (TDLAS) signal when that signal undergoes amplitude variations caused by process flow variations (e.g. dust, density gradients, and other time-varying transmission losses) or by measurement noise. A model is developed which accounts for noise sources from (a) laser intensity fluctuations, (b) process flow variations, and (c) electronic and detection system noise. The model is used to derive an optimal signal-averaging scheme for both noise sources and the generic case combining both noise sources. A weighted average is calculated based on the model parameters and parameters of the measured shot-by-shot TDLAS signal and is used to reduce the measurement noise below that which is achieved using traditional equal-weighted averaging. In this way, the performance (e.g. precision and accuracy) of the TDLAS or other spectroscopic instrument can be enhanced in harsh environments where process flows induce large transmission changes and when the instrument is used to measure data near its limits of detectability (LOD).

Why Performing Pre-Processing

In spectroscopic measurement, for example with TDLAS, the raw data representing the light received by the photo-detector can contain strong noise and artifacts due to fast transmission fluctuations. Clearly, these data should not be fed directly to the curve fitting algorithm for quantitative analysis of the gas concentration, but a carefully selected pre-processing is necessary to reduce the noise and remove unwanted artifacts.

Figure 1:
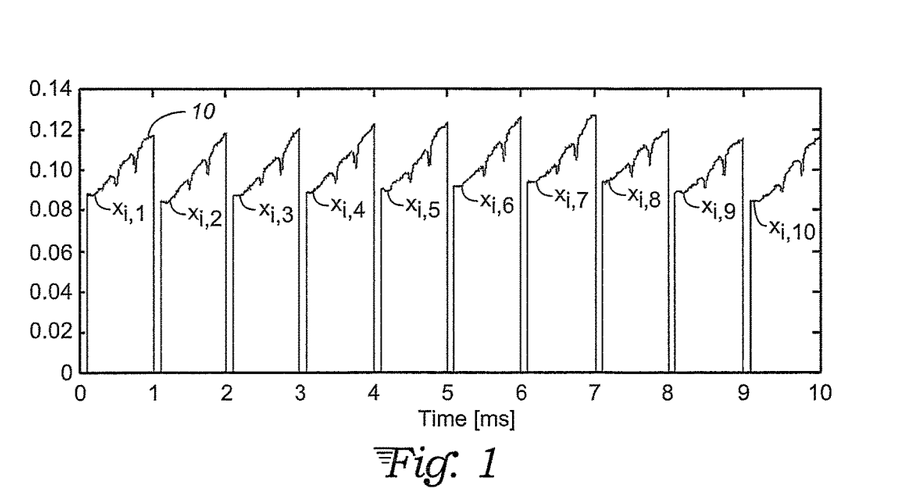
FIG. 1 shows a graph of sensed light amplitude versus time representing raw data from a TDLAS instrument collected over ten successive wavelength scans.

An instance of the raw data collected from a TDLAS instrument is shown in FIG. 1. Clearly, one frequency scan 10 in FIG. 1 lasts 1 ms. On the other hand, the gas analysis must be performed, at most every 100 ms-1 s. Therefore, a possible way for increasing the signal to noise ratio and removing artifact is by performing a form of averaging of the raw data. Let us denote with $\{x_{i,j}\}$ for $i=1, \ldots, N$ and $j=1, \ldots M$ the TDLAS raw data. In particular $x_{i,j}$ represents the $i^{th}$ samples of the light received by the photodetector during the $j^{th}$ scan. N represents the number of samples per scan, while M the number of scans. Given the raw data $\{x_{i,j}\}$, the goal is to design the weights $\{w_{i,j}\}$ such that the averaged data, denoted as $\bar{x}_i$ defined as follows $$\bar{x}_i = \Sigma_{j=1}^{M} w_{i,j} x_{i,j} \qquad (1)$$

have maximal signal-to-noise ratio and contain no artifacts. After the pre-processing step, the averaged signal is ready to be fed into the signal processing scheme in which the curve fitting and the concentration determination are performed.

On top of the electrical noise (due to both TDLAS transmitter and receiver), it has been shown that dust present in the duct will cause transmission fluctuations. As a consequence, the ramps may not only have a different amplitude but some of the ramps may even be strongly distorted by fast transmission fluctuations. It is not obvious whether ramps with low amplitudes should be simply added or down-weighted with respect to ramps having large amplitude. Moreover, it is not immediately clear whether, it is appropriate to discard or down-weight heavily distorted ramps. In the ensuing sections, these alternatives are explored and the performances obtained using several pre-processing schemes are assessed.

Weighted, Average Based on Signal Amplitude

Figure 2:
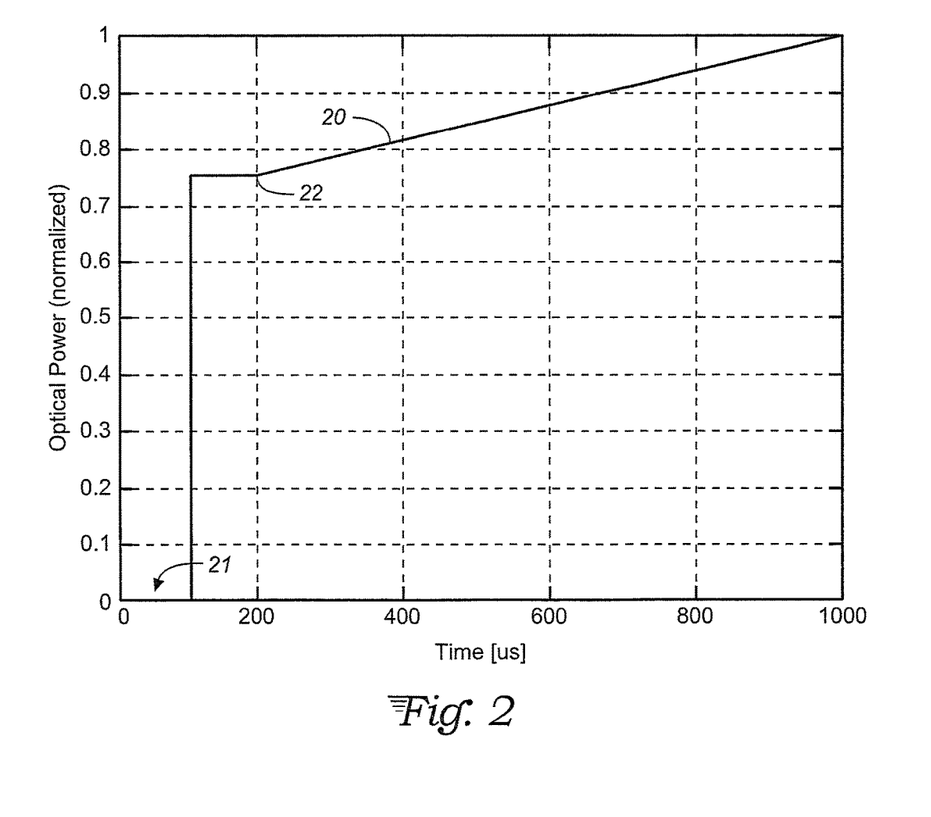
FIG. 2 shows a graph of optical power generated by a TDLAS laser, normalized by its maximum power, versus time for a single transmitted ramp.

The electrical ramp signal 20 delivered to the laser driver is shaped to have two constant plateaus 21 and 22 which can be used to evaluate the ramp offset and amplitude. An instance of the transmitted ramp is depicted in FIG. 2. (In principle, the ramp structure could be changed, and in fact, the second plateau 22 could be avoided in some embodiments.)

As shown in FIG. 1, after light transmission and detection, different scans might have different offsets and different amplitudes. Given the raw data, the offsets of each scan can be calculated via the first plateau since the laser, during this time, will not transmit light. The offset of the $j^{th}$ scan is calculated as follows:

$$o_j = \frac{1}{i_{1,stop} - i_{1,start} + 1} \sum_{i=i_{1,start}}^{i_{1,stop}} x_{i,j},$$

Where $i_{1,start}$ and $i_{1,stop}$ are the sample index where the first plateau start and stop, respectively. Successively, the offset can be removed as follows:

$$x_{i,j}' = x_{i,j} - o_j$$

After having calculated and removed the offset, the amplitude of each ramp can be estimated by calculating the average amplitude of the second plateau. Denoting $A_j$ the amplitude that is experienced by the scan j, $A_j$ can be calculated as follows:

$$A_j = \frac{1}{i_{2,stop} - i_{2,start} + 1} \sum_{i=i_{2,start}}^{i_{2,stop}} x_{i,j}',$$

where $i_{2,start}$ and $i_{2,stop}$ are the sample index where the second plateau start and stop, respectively. From now on, the amplitude of each ramp can be considered known.

Assuming further that this amplitude keeps constant over the duration of the ramp, the effect of simple average, multiplied average and normalized average on the signal variance is assessed. In synthesis, it holds that the pursuit of the optimal weighting scheme depends on the source of noise. In particular, if we assume that the major noise contribution is additive to the acquired ramp (due to additive electronic noise at the detector or due to fluctuations), the optimal averaging scheme is to weigh the ramp by the respective signal amplitude, i.e., ramps with large amplitude will contribute more to the average than ramps with small amplitude, which are down-weighted. The analysis can also predict the expected loss in variance if the simple average scheme is used instead of the weighted average scheme. It is worth pointing out here that this loss can be very minimal especially if the signal amplitude does not significantly vary among different ramps.

In synthesis, we can identify three schemes of weighting based on signal amplitude (It is worth pointing out here that the weights do not necessarily have to sum to 1, since, eventual multiplication factors can be compensated by the successive block of baseline fitting.):

W1) Simple Average
The weights in the eq. (1) are defined as follows:

$$w_{i,j}=1$$

This represents the conventional approach of the prior art.

W2) Multiplied Average
The weights in the eq. (1) are defined as follows:

$$W_{i,j}=A_j \text{ for each } i=i_{r,start}, \ldots, N$$

where $i_{r,start}$ is the index wherein the linear ramp starts. The multiplied average weights are optimal when the noise is additive, i.e., noise due to fast fluctuation due to dust or electronic noise.

W3) Normalized Average
The weights in the eq. (1) are defined as follows:

$$W_{i,j}=\frac{1}{A_j} \text{ for each } i=i_{r,start}, \ldots, N$$

The normalized average weight is optimal in case the additive noise can be neglected and the noise is dominated by change in absorbance, i.e., pressure, effective path length, temperature, and concentration.

Weighted Average Based on Signal Similarity

As anticipated, fast and strong fluctuations might heavily distort a single ramp signal. The question to answer is whether to discard/down-weight distorted ramps or not. Several weighting schemes for down-weighting distorted ramps can be envisioned. In particular, a heuristic approach that has been found effective, is to calculate the distance among consecutive ramps (discarding the points of the two plateaus). The distance is calculated in the L2 norm sense, i.e. the points of two consecutive ramps are subtracted, the difference vector is than squared, and the squared differences are summed up. More precisely, given a certain ramp, the distances with respect to the previous and subsequent ramps are calculated, and summed up. The weight is then the inverse of this quantity. In fact, if the distances of the current ramp with respect to the previous and subsequent ramps are small, the weight to the ramp in the average will be large. On the other hand, if the ramp is very distant from the adjacent ramps, then the weight will be small and the ramp contribution in the average is small.

In synthesis, we can identify two schemes of weighting based on signal similarity:

W4) Weights Inverse Distance
The weights in the eq. (1) are defined as follows:

$$w_{i,j}=\frac{1}{\sum_{i=i_{r,start}}^{N}(x'_{i,j}-x'_{i,j-1})^2 + \sum_{i=i_{r,start}}^{N}(x'_{i,j}-x'_{i,j+1})^2}$$

for each $i=i_{r,start}, \ldots, N$. Clearly $\sum_{i=i_{r,start}}^{N}(x_{i,j}'-x_{i,j-1}')^2$ is the square Euclidean distance between the $j^{th}$ and $(j-1)^{th}$ ramps, while $\sum_{i=i_{r,start}}^{N}(x_{i,j}'-x_{i,j+1}')^2$ is the square Euclidean distance between the $j^{th}$ and $(j+1)^{th}$ ramps. Numerical tests have shown that the Weights inverse distance selection improves the performance in presence of fast fluctuation due to, e.g., dust.

W5) Weights Inverse Local Distance
The weights in the eq. (1) are defined as follows:

$$v_{i,j}=\frac{1}{(x'_{i,j}-x'_{i,j-1})^2 + (x'_{i,j}-x'_{i,j+1})^2} \text{ for each } i, j \text{ and}$$

$$w_{i,j}=\frac{v_{i,j}}{\sum_{j=1}^{M}v_{i,j}}$$

The main difference of W4 and W5 is that, if one ramp contains a large outlier, in the W4 case, the whole ramp is down-weighted, while in the W5 case, only the sample containing the outlier and the adjacent points are down-weighted.

Remark:
In principle, the averaging rules W4 and W5 could be applied to the original signal $x_{i,j}$ instead of $x_{i,j}'$. In addition, the same rules could be applied to the standardized raw data (the raw data after offset removal and normalization), that is, $$x''_{i,j}=\frac{x'_{i,j}}{A_j}$$

Finally, the weighted average based on signal similarity can also be combined with the weighted average based on signal amplitude. Here, the total weight can be evaluated by, e.g. multiplication of the weights based on signal amplitude and on signal similarity.

For the facilitating IP protection, we could also include a general case, defined as follows:

W6) General Weights $$w_{i,j}=f\left(\{x_{i,j}\}_{\substack{i=1,\ldots N \\ j=1,\ldots N}}\right)$$

Simulation Results
Pre-Processing Results Obtained with Weighted Average Based on Signal Amplitude We have performed a quantitative analysis of the resulting concentration variance versus modulation frequency and averaging scheme. The performance is measured in terms of concentration variance. One important implementation trick was the utilization of a warm start, i.e., the previous (averaged) ramp parameters calculated by the curve fitting are fed as starting point of the new curve fitting for the next averaged ramp. For this procedure to be effective, the ramp is normalized by the second plateau level before being fed to the curve fitting algorithm.

Figure 3:
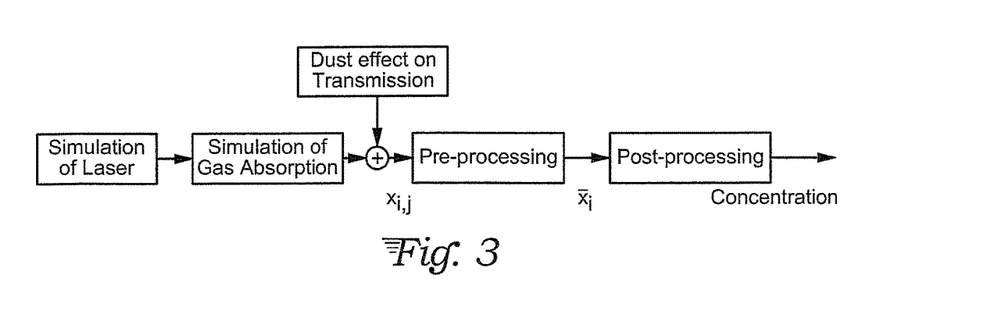
FIG. 3 is a block diagram of a simulation of the overall procedure, which represents the basic approach applicable to TDLAS or other spectroscopic instruments employing the present invention.
Figure 4:
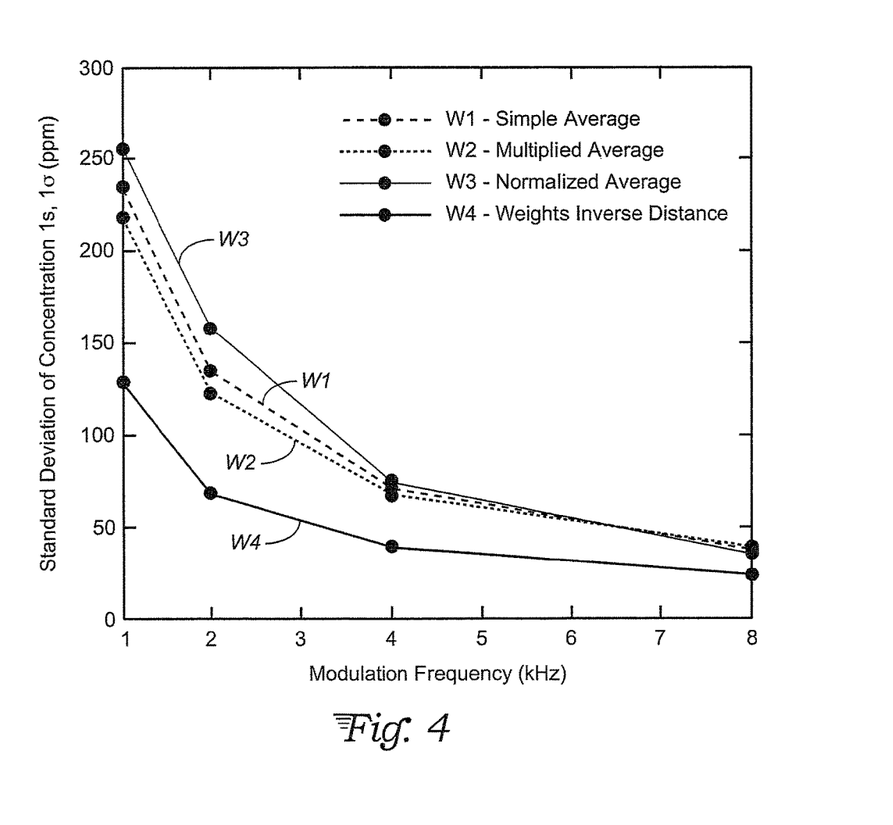
FIG. 4 is a graph of performance of different averaging approaches (simple average, multiplied average, normalized average, weights inverse distance) in terms of standard deviation of concentration (ppm) versus modulation frequency (kHz).

The block scheme of our simulation is depicted in FIG. 3. FIG. 4 shows the concentration variance versus modulation frequency for the simple W1, normalized W3, and weighted averaging schemes W2 and W4. Increasing the modulation frequency, as expected, has a positive influence on the concentration variance since it significantly decreases. As expected, the multiplied average W2 is the most promising strategy, but the improvement with respect to the simple average W1 is only minimal, and the performance of all averaging schemes coincides for high modulation frequencies (i.e., 8 kHz).

In conclusion, with the current dust transmission data, the gain of the multiplied average scheme with respect to simple averaging is only minimal (i.e., 5%), while the two schemes perform almost identically at 8 kHz. These results indicate the effectiveness of performing additional weighted averaging based on signal similarity.

Spectroscopic Instrument and Measurement Process

Figure 5:
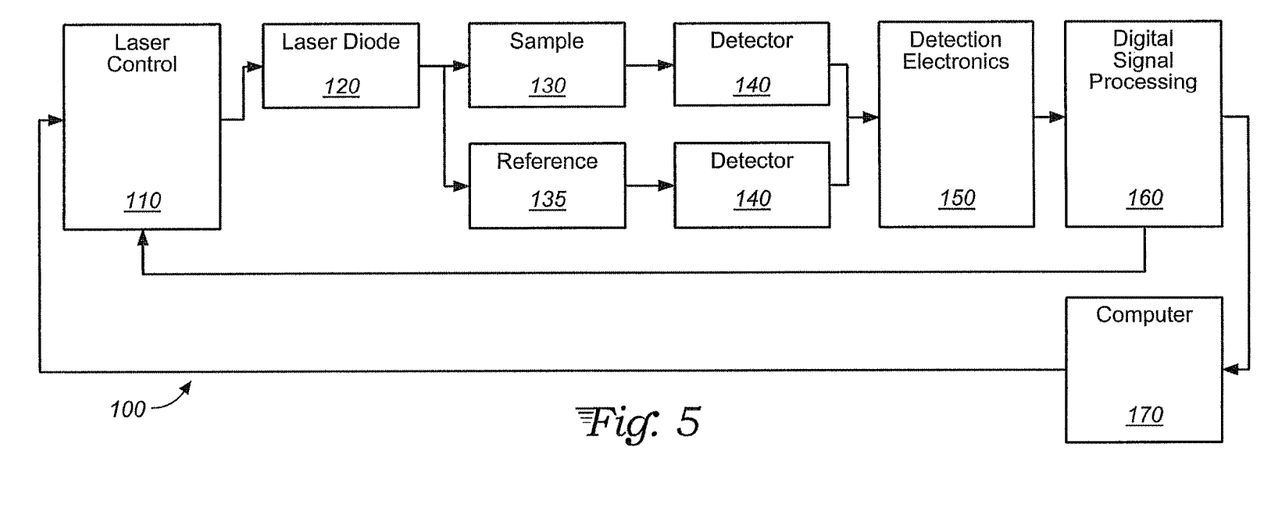
FIG. 5 illustrates an embodiment of a tunable diode laser absorption spectroscopy (TDLAS) system.

With reference to FIG. 5, a spectroscopy system 100 capable of employing the signal pre-processing scheme according to the present invention may include a laser control module 110, laser diode(s) 120, sample chamber 130 and (optional) reference chamber 135, corresponding detectors 140 and detection electronics 150, a digital signal processing module 160 and a computer 170. System 100 thereby provides for spectroscopy measurements of samples in comparison with control substances and for recording and display of results. Of particular interest are the digital signal processing module 160 and computer 170 that process spectroscopic data received from the detection electronics 150 in the manner described below.

Laser control module 110 controls one or more laser diodes 120. Laser diodes 120 are tunable laser diodes, providing for a range of outputs. Sample chamber 130 receives a sample, typically in a gaseous or vapor form, for evaluation. If provided in the system, a reference chamber 135 similarly receives a reference substance or reference sample for evaluation in comparison to the sample of sample chamber 130. Laser diodes 120 are arranged to illuminate sample chamber 130 and reference chamber 135, such as through an arrangement of mirrors, lenses and windows (not shown), repeatedly sweeping through a specified range of wavelengths over a period of time. Detectors 140 are positioned to receive light from laser diodes 120 after the light passes through the sample chamber 130 (and optional reference chamber 135) and after the light has undergone wavelength-specific absorption by atomic or molecular species present in the chamber(s). Thus, detectors 140 detect presence of specific atoms or molecules in reference chamber 135 and sample chamber 130 responsive to light from laser diodes 120. Arrangement and construction of laser diodes 120, chamber 130 and 135 and detectors 140 is well understood to those having skill in the art.

Detection electronics 150 operate detectors 140 and record data received from detectors 140 in raw format. Digital signal processing module 160 processes raw sample data from the detection electronics 150 in the manner described below to extract usable measurement data while removing or substantially reducing various noise contributions present in the raw data. Computer 170 controls operation of the digital signal processing module 160 and laser control module 110, as well as possibly other parts of the system 100, such as the mirrors, lenses and windows mentioned above, and flow of sample materials into chambers 130 and 135, and thereby controls operation of the overall system 100.

Division of processing between detection electronics 150, digital signal processing module 160 and computer 170 may vary depending on exact implementations in various embodiments. However, one may expect these three modules to collectively perform processes related to recording data, processing raw sample data into measurement data. Moreover, computer 170 may be expected to store data points in various formats (raw sample data and processed measurement data) for longer-term storage and display purposes. Digital signal processing module 160 may include a signal digital signal processor (DSP) such as those available from Texas Instruments for example. Digital signal processing module 160 may include more elaborate components such as multiple DSPs and related components.

Figure 6:
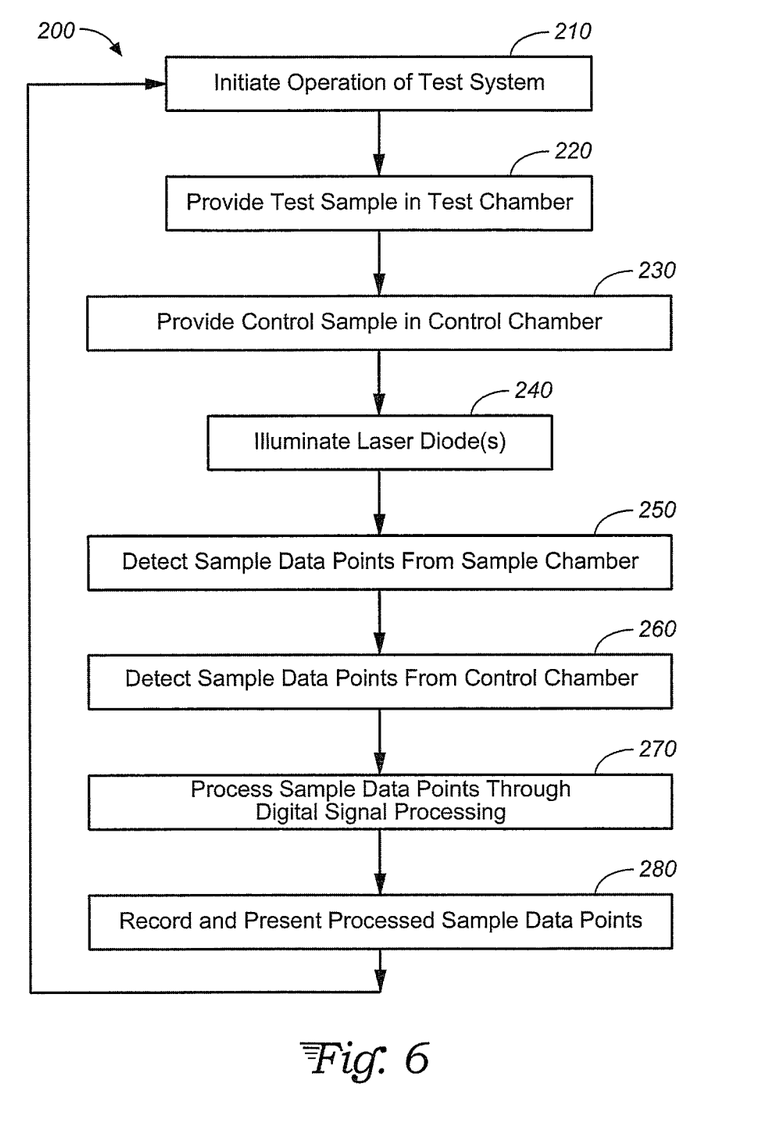
FIG. 6 illustrates an embodiment of a process of measuring using a TDLAS system, the process being adaptable to incorporation of the weighted averaging scheme of the present invention in step 270.

A process 200 like that in FIG. 6 may be implemented by any spectroscopic system, such as the system 100 of FIG. 5, or a similar system using tunable laser diodes or other tunable lasers, or even a broad spectrum instrument with wavelength separation onto multiple detectors. The result, however obtained, is raw sample data representing wavelength-specific optical absorption over some wavelength range, where measurement noise may be present from any of additive electronic detector noise, laser intensity fluctuations, density gradients or dust in the sample flow, or small fluctuations in the underlying absorption due to pressure and temperature variations of the sample. The raw sample data is processed to remove or reduce as much of the measurement noise as possible in order to obtain usable measurement data.

Process 200 may generally include initiating operation 210 of a spectroscopy instrument, providing a test sample (220) and perhaps also a control sample (230), illuminating laser diodes 240, which may be driven to produce a series of sweeps over a specified range of wavelengths, detecting sample data points (250, 260), pre-processing the sample data 270 according the method of the present invention to remove noise contributions, and recording and presenting processed data points 280. Various steps of the process 200 may be executed or implemented in a variety of ways, whether by a pre-programmed machine, a specialized machine, or a set of machines.

Initiating the operation in step 210 may include any warm-up and calibration procedures that may be necessary, along with possible preparation and placement of samples (depending on their source). For example, some components may need to be set to a controlled temperature for preferred operation, and chambers may need to be pumped down to near-vacuum. Step 220 (and optional step 230) may involve the flowing of a gaseous (or vaporized) test sample into the spectroscopy instrument's test chamber, and likewise flowing gaseous (or vaporized) control sample into any parallel control chamber that the instrument may have.

In step 240, measurement can begin, as the laser diode(s) are illuminated. This may involve simply illuminating a single tunable laser diode, or may turn on different laser diodes in a series fashion for different wavelength bands, or may involve illuminating multiple laser diodes simultaneously with subsequent wavelength-separation of the light within the spectrometer toward different detectors. Responsive to step 240, raw data points are detected from the sample chamber (and the reference chamber) in step 250 (and optional step 260), based on absorption of the laser light as it passes through the sample gas in the respective chambers. These raw data points are recorded at the time of detection.

At step 270, the raw data points are processed through digital signal processing to provide measurement data, which may be normalized, for example, or otherwise adjusted for any known systematic effects upon the measurement. This also includes a weighted averaging in a manner according to the present invention that minimizes various possible noise contributions to the data. In step 280, the processed measurement data is stored, analyzed, displayed and the like, as required by a user.

While conventional use of a TDLAS system or other spectroscopic instrument is well understood with regard to FIG. 6, opportunities for better noise modeling and calibration exist, in particular in relation to step 270. To understand an approach implemented in various embodiments herein, it may be useful to start with mathematical background for a potential calibration process.

Let $I_0(v)$ and $I_k(v)$ denote the light emitted by the laser and the light detected at the photodetector at wavenumber v during the kth scan, respectively, for k=1, K where K represents the total number of scans. According to the Beer-Lambert law, it holds that $$I_k(v) = I_0(v)e^{-A(v)} \quad (2)$$

where A(v) is the absorbance at wavenumber v, and it is assumed to be constant with the scan index. Since $A(v) \approx 0$, a first-order Taylor expansion of the exponential function in (2) yields $$I_k(v) = I_0(v)[1 - A(v)] \quad (3)$$

Unfortunately, (3) is only an abstraction and in practical cases several disturbances impair it. In fact,
1. additive detector noise is typically present in $I_k(v)$. Let us denote such noise as $e_k(v)$;
2. small fluctuations of the true underlying absorption can occur due to, e.g., pressure and temperature variations. Let us denote such noise as $v_k(v)$;
3. variation in the signal amplitude can occur due to either or both laser intensity fluctuations and physical perturbations, e.g., dust or density gradients in the flow. Let us assume that this amplitude fluctuation is independent of n and let us denote such amplitude as $c_k$.

A possible model that includes the three disturbances mentioned above is given as follows:

$$I_k(v) = C_k I_0(v)[1 - A(v) + v_k(v)] + e_k(v); \quad (4)$$

Denoting $T(v) := [1 - A(v)]I_0(v)$, the model in (4) can be rewritten as $$I_k(v) = C_k[T(v) + I_0(v)v_k(v)] + e_k(v); \quad (5)$$

One can expect that the gain $C_k$ is known for each k. This knowledge can be achieved, e.g., by enabling the laser to send a constant plateau where the current is kept constant and by averaging the raw detected light during this constant interval. It is important to guarantee that there is no absorption at the wavenumber of the plateau.

One can focus on a specific wavenumber, $v^*$, and drop the wavenumber index for notation simplicity. The averaging goal is to find, the optimal weights $\{w_k\}_{k=1}^{K}$ such that the estimator $\hat{I} := \sum_{k=1}^{K} w_k I_k$ is unbiased and has minimum variance. To carry out the analysis, one can assume that both $e_k$ and $v_k$ are normally distributed around 0, i.e., $e_k \sim N(0, \sigma_0^2)$, $v_k \sim N(0, \sigma_f^2)$, and that both noises are independent. Let us also define $\sigma_v^2 := I_o^2 \sigma_f^2$.

Optimal Averaging Scheme

Using (5), it holds that $$\sum_{k=1}^{K} w_k I_k = \left(\sum_{k=1}^{K} w_k c_k\right) T + \left(\sum_{k=1}^{K} w_k c_k I_0 v_k\right) + \left(\sum_{k=1}^{K} w_k c_k\right) \quad (6)$$

since $e_k \sim N(0, \sigma_0^2)$ and, $v_k \sim N(0, \sigma_f^2)$, it holds that $$T \sim N\left(\left(\sum_{k=1}^{K} w_k c_k\right) T, \sum_{k=1}^{K} w_k^2 (C_k^2 \sigma_v^2 + \sigma_v^2)\right) \quad (7)$$

Therefore, the problem of finding the minimum unbiased estimator can be cast as the following optimization problem:

$$\{\hat{w}_k\}_{k=1}^{k} := \underset{\{w_k\}_{k=1}^{k}}{\arg \min} \sum_{k=1}^{k} w_k^2 (C_k^2 \sigma_v^2 + \sigma_v^2) \quad (8)$$

$$\text{subject to } \sum_{k=1}^{k} w_k c_k = 1.$$

To solve equation (8), we can resort to Lagrangian optimization. Writing the Lagrangian of the problem in (8) yields $$L(\{w_k\}_{k=1}^{k}, \lambda) := \sum_{k=1}^{k} w_k^2 (C_k^2 \sigma_v^2 + \sigma_v^2) + \lambda \left(\sum_{k=1}^{k} w_k c_k - 1\right) \quad (9)$$

The partial derivatives of the Lagrangian are as follows $$\frac{\partial L}{\partial w_k}(\{w_k\}_{k=1}^{k}, \lambda) = 2w_k(C_k^2 \sigma_v^2 + \sigma_e^2) + \lambda C_k \quad (10)$$

and $$\frac{\partial L}{\partial \lambda}(\{w_k\}_{k=1}^{k}, \lambda) = \sum_{k=1}^{k} w_k C_k - 1 \quad (11)$$

Setting $$\frac{\partial L}{\partial w_k}(\{w_k\}_{k=1}^{k}, \lambda)$$

to zero yields the solution $$\hat{w}_k = -\lambda \frac{C_k}{2(C_k^2 \sigma_v^2 + \sigma_e^2)} \quad (12)$$

Substituting the solution of (12) into (11) and setting to zero yields $$\hat{\lambda} = -\frac{1}{\sum_{k}^{K} \frac{C_k^2}{2(C_k^2 \sigma_v^2 + \sigma_e^2)}} \quad (13)$$

Substituting (13) into (12) yields the following optimal weights:

$$\widehat{w_k} = \frac{C_k}{(C_k^2 \sigma_v^2 + \sigma_e^2) \sum_{k'=1}^{K} \frac{C_{k'}^2}{2(C_{k'}^2 \sigma_v^2 + \sigma_e^2)}} \quad (14)$$

Next, we will analyze two cases of special interest.

Detector Noise Model

Under the assumption that the detector noise dominates the absorbance noise, it holds that $\sigma_v^2$ can be set to zero with minimal error. In this case (14) becomes $$\widehat{w_k} = \frac{C_k}{\sum_{k'=1}^{K} C_{k'}^2} \quad (15)$$

From (15), it holds that, in presence of detector noise only, the optimal strategy is to weight more heavily traces that have larger $C_k^2$. Note that the term $\Sigma_{k=1}^{K} C_k^2$ is just a constant that can be neglected if a multiplicative baseline is fitted.

Indeed, under this choice of the weights, the overall variance of the averaged trace $\bar{I}$ is $$\frac{\sigma_v^2}{\sum_{k=1}^{K} C_k^2}$$

Observe that a simple unweighted sum will end up with a variance of $$\frac{K}{(\Sigma_{k=1}^{K} C_K)^2} \sigma_e^2$$

which is uniformly larger than $$\frac{\sigma_v^2}{(\Sigma_{k=1}^{K} C_k)^2}.$$

Fluctuation Noise Model

Under the assumption that the detector noise can be neglected, i.e. $\sigma_v^2 = 0$, it holds that (16).

$$\widehat{w_k} = \frac{1}{KC_K}$$

From (16), it holds that, in absence of detector noise the optimal strategy is to down-weight traces that have larger $C_k$.

Under this choice of the weights, the overall variance of the averaged trace $\bar{I}$ is $$\frac{\sigma_v^2}{K}.$$

Observe that an unweighted sum produces a variance of $$\frac{\Sigma_{k=1}^{K} C_k^2}{(\Sigma_{k=1}^{K} C_k)^2} \sigma_v^2$$

which is uniformly larger than $$\frac{\sigma_v^2}{K}.$$

It is thus shown that the optimal averaging strategy depends on the type of noise expected in the analyzer system. If the detector noise is negligible, the received signal should be normalized by amplitude. On the other hand, if the detector noise dominates, the received signal should be multiplied by the amplitude.

If both effects contribute significantly, the optimal weights are given by (14).

Weighted Average Based, on Similarity to Adjacent Signals in the Time Series

In addition to assigning a weight to each TDLAS trace based upon single-trace characteristics (e.g. based upon the single-trace amplitude Ck), the weighting factor can be assigned based upon the similarity or differences of each signal to the prior and following signals in the continuous time series. Fast changes in signal amplitude are caused by process changes (e.g. a large dust particle or turbulent eddy) and can heavily distort a single ramp signal. Particularly if the process changes occur on a time scale faster than the repetition rate of the TDLAS signal, a simple amplitude weighting can fail to reject low-quality signals. Several weighting schemes based upon prior and following traces can be envisioned. In particular, a heuristic approach that has been found to be effective is to calculate the deviation between consecutive ramps. In this approach, the difference between two traces is calculated, the difference vector is squared, and the squared differences are summed. The weight is then the inverse of this quantity. This quantity can be computed based upon the difference with traces adjacent in time either before, after, or including both before and after the current TDLAS signal. This scheme can be combined with the weighted average based upon signal amplitude outlined in Equations (14), (15) and (16). Here, the total weight can be evaluated by e.g. multiplication of the weights based on signal amplitude and on signal similarity.

A weighted averaging scheme that uses the weights prescribed by Equations (14), (15) and (16) can be implemented as part of the signal processing algorithm for a tunable diode laser absorption spectroscopy (TDLAS) sensor. This weighted averaging scheme reduces sensor noise and improves sensor performance in many cases, including dusty or turbulent environments, as compared to a simple unweighted average as used by other absorption sensors. In order to implement this strategy, three steps must be undertaken: (1) determine the amplitude fluctuation of each trace $C_k$; (2) calculate a weighting factor for each trace using the appropriate choice of the above strategies; and (3) calculate a weighted average of the traces using the prescribed weights. The amplitude fluctuation, $C_k$, for each trace can be determined via multiple strategies including:

Peak-to-peak signal amplitude

Signal amplitude at a specific point or during a specific duration of time in the TDLAS trace Signal amplitude at a specific point or during a specific duration of time in the TDLAS trace, minus any background signal (determined during a time when the laser is disabled)

Slope of the ramp portion of the TDLAS signal

Using the determined amplitude of each trace $C_k$, from one of the above strategies, the user can determine if Equation (14), (15) or (16) is appropriate to calculate the optimal weighting coefficients based upon the known noise sources of the instrument, and apply the weighting coefficient as part of a weighted average calculation before passing the data to the signal processing module.

Summary of Choice of Optimal Weighting Coefficients

Modeling the optimal weighting coefficient for each laser scan by choosing the appropriate one of:

For the case where the noise is dominated by electronic sources independent of the measured volume, the optimal weighting coefficients are given by the equation:

$$\widehat{w_k} = \frac{C_k}{\Sigma_{k=1}^{K} C_k^2}$$

For the case where the noise is dominated by changes in the measurement volume, the optimal weighting coefficients are given by the equation:

$$\widehat{w_k} = \frac{1}{KC_k}$$

For the general case, including both sub-cases above, the optimal weighting coefficients are given by the equation:

$$\widehat{w_k} = \frac{C_k}{(C_k^2 \sigma_v^2 + \sigma_e^2)\Sigma_{k'=1}^{K} \frac{C_{k'}^2}{2(C_{k'}^2 \sigma_v^2 + \sigma_v^2)}}$$

The general case is normally used only where neither particular noise source dominates.

In each of the above equations, $\widehat{w_k}$ is the optimal weighting coefficient, CK is the amplitude of each laser scan k, $\sigma_v^2$ is the variance of the electronic noise source, and $\sigma_v^2$ is the variance of the noise source within the measurement volume.

Which types of noise are dominant in a measurement, and consequently which weighting scheme is optimal, is typically known a priori based upon the application. For an application with a laser having low power or one carried out in a relatively clean environment (not a lot of dust, transmission losses, etc.) we would expect the system noise to be dominated by electronic noise. This is actually a very small number of the potential applications. For most applications, the dust and transmission noise will dominate, and we would use the fluctuation noise model.

Figure 7:
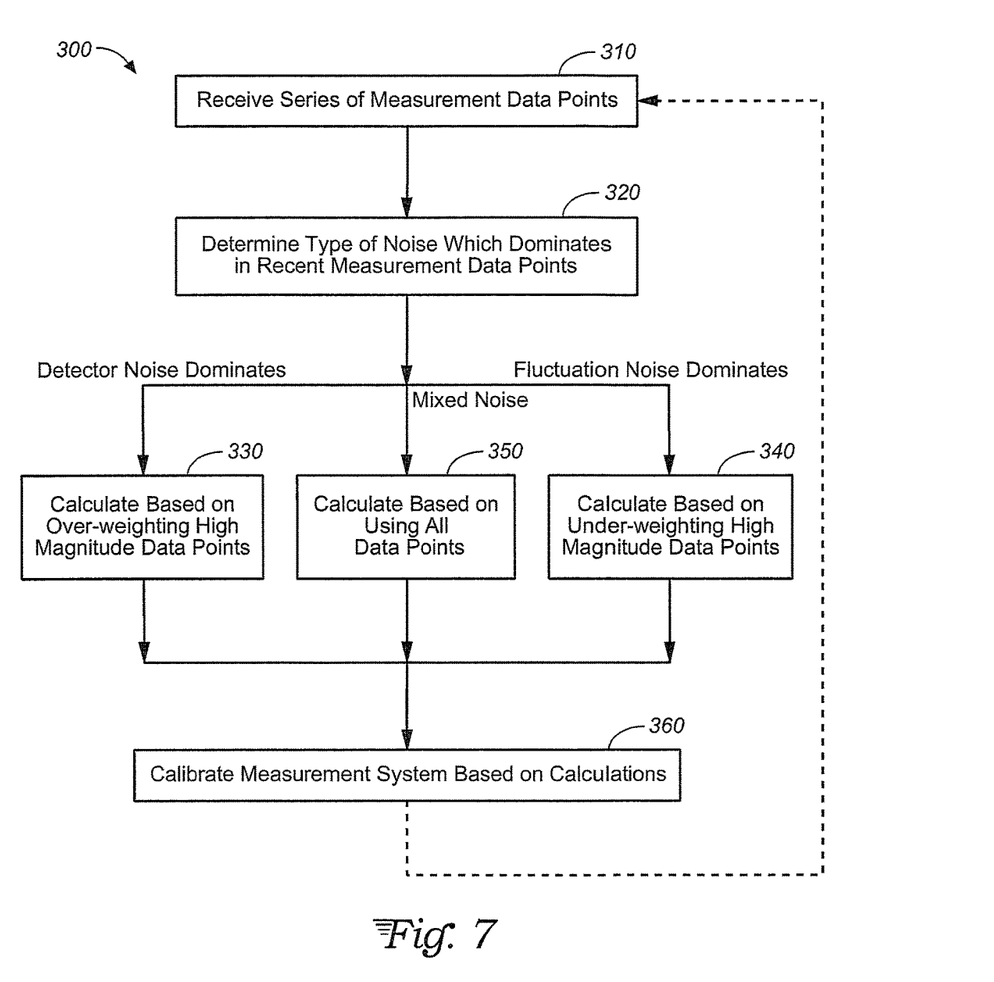
FIG. 7 illustrates an example of a process of pre-processing the raw data from a TDLAS system in accord with the present invention.

Using this spectroscopy system, one can improve operation and measurements results of an embodiment such as that of FIG. 5. FIG. 7 illustrates a process in accord with the present invention of pre-processing the raw data from a TDLAS system for effecting noise reduction in the data. Process 300 includes receiving data points (310), determining types or noise likely present in data points (320), calculating parameters for calibration (330, 340 and 350), and calibrating the measurement system (360). Data points in a raw, sample or measurement format come from the system at module 310. The data points may come in more than one format, allowing for determination of what processing has occurred. A determination is made at step 320 as to whether the type of noise in the data points primarily represents detector noise, fluctuation noise, or a mix of the two types of noise.

Depending on the results of this determination 320, different calculations of weighting coefficients for the signal averaging are made. If detector noise dominates, then high magnitude data points are over-weighted in step 330 as with equation (15). If fluctuation noise dominates, then low magnitude data points are over-weighted in step 340 as with equation (16). If neither type of noise dominates, a more general approach to calculating coefficients is used in step 350 as with equation (14). The averaging calculations are then made at step 360 based on the weighting coefficients from one of the steps 330, 340 and 350. Note that the determination in step 320 may be made based on review of data points provided to the process. 300, or it may be made based on user review and input, for example.

Figure 8:
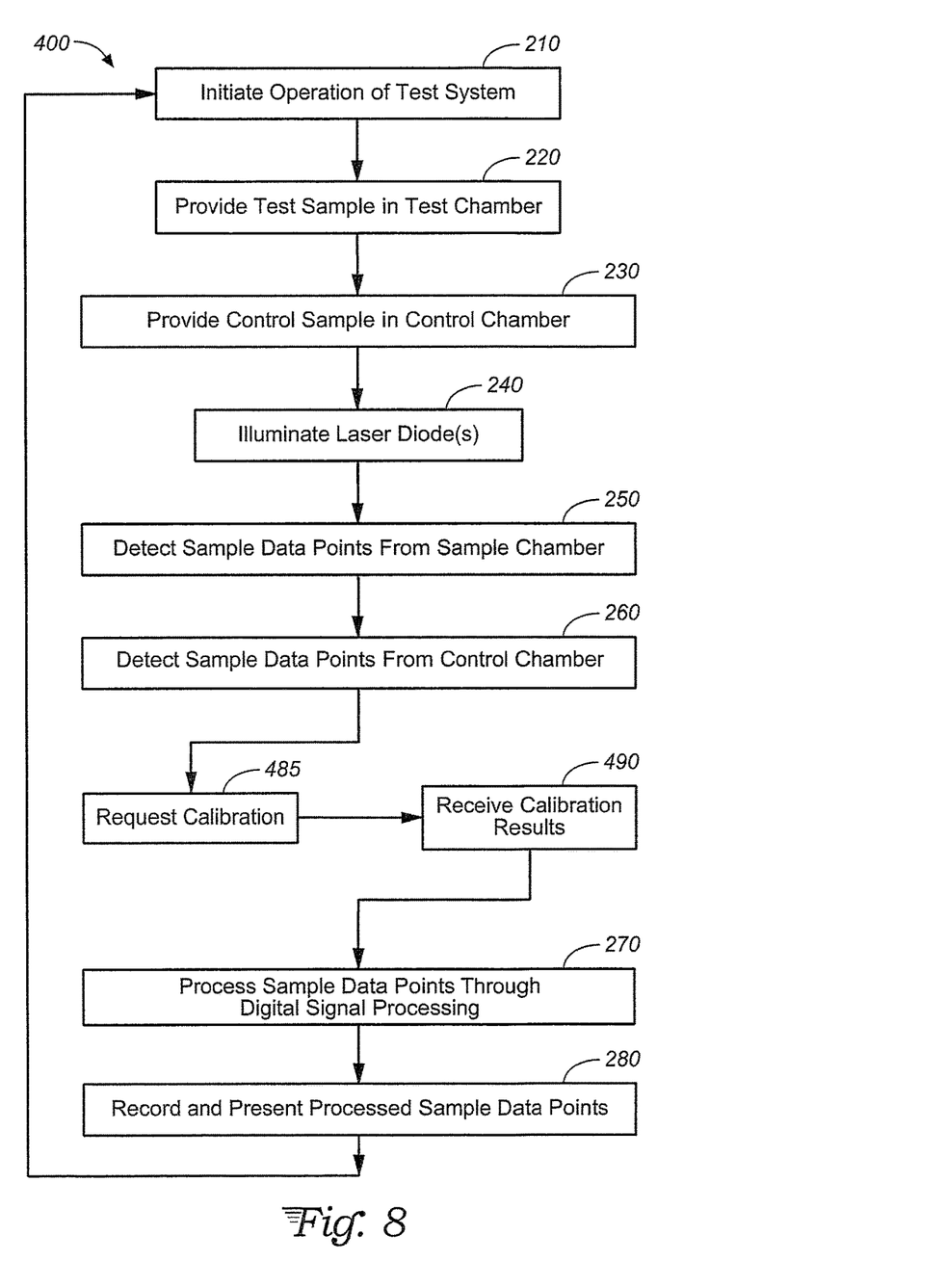
FIG. 8 illustrates an embodiment of a process of operating a TDLAS system using the data pre-processing of FIG. 7.

FIG. 8 illustrates an embodiment of a process of operating a TDLAS system using the measurement process of FIG. 7. Process 400 includes the basic modules or steps of process 200 of FIG. 6, along with additional operations. Process 400 further includes pre-processing calibration or noise reduction request 485 for the raw data and pre-processing calibration results 490.

Process 400 operates the TDLAS system as with process 200, processing module 210 through 260, thereby supplying samples, illuminating the samples and collecting data. However, process 400 then requests calibration or raw data pre-processing at step 485, invoking a weighted averaging process such as that of process 300 of FIG. 7. At step 490, calibration results from that averaging are received by the process 400, such as through a signal that the system has been calibrated with adjusted parameters, for example, or a signal to enter adjusted parameters in the system based on calibration. At step 270, the pre-processed measurement data is further processed or analyzed. This may involve only processing new (i.e., changed) data as the spectroscopic system continuously operates. However, it may also involve re-processing and re-presenting older raw or pre-processed data (e.g., using a moving averages scheme), thereby re-evaluating or constantly updating such data and potentially providing a more correct or up-to-date result than was originally achieved with earlier measurements and analyzing such updated data. The process also records and presents the processed data sample points at module or step 280, with or without additional analysis results, for example, visually on a computer display.

What is claimed is:

1. A method of measuring absorption using a spectroscopic instrument, the method comprising:

initiating absorption measurements with the spectroscopic instrument and receiving a series of raw intensity measurement data points from at least one detector of the spectroscopic instrument;

determining if detector noise or fluctuation noise dominates in the series of raw intensity measurement data points;

calculating, by a digital signal processor and based on the determination, a set of weighting coefficients for the raw intensity measurement data points, wherein greater weight is given to larger intensity raw measurement data points over smaller raw intensity measurement data points when detector noise dominates, and wherein greater weight is given to smaller intensity raw measurement data points over larger intensity raw measurement data points when fluctuation noise dominates; and performing, by the digital signal processor, a weighted averaging upon the raw intensity measurement data points using the calculated set of weighting coefficients to output from the spectroscopic instrument a set of pre-processed measurement data that is characterized by reduced noise contributions.

2. The method as in claim 1, further defined by continuously operating the spectroscopic instrument to successively receive new raw intensity measurement data points with the same or updated weighting coefficients, and performing updated weighted averaging calculations with the new raw intensity measurement data points to output updated pre-processed measurement data.

3. The method of claim 1, wherein calculating the set of weighting coefficients and performing the weighted averaging of the raw intensity measurement data points applies weights $$\widehat{w_k} = \frac{C_k}{\Sigma_{k'=1}^{K} C_{k'}^2}$$

when detector noise dominates.

4. The method of claim 1, wherein calculating the set of weighting coefficients and performing the weighted averaging of the raw intensity measurement data points applies weights $$\widehat{w_k} = \frac{1}{KC_K}$$

when fluctuation noise dominates.

5. The method of claim 1, wherein calculating the set of weighting coefficients and performing the weighted averaging of the raw intensity measurement data points applies weights $$\widehat{w_k} = \frac{C_k}{(C_k^2 \sigma_v^2 + \sigma_s^2)\Sigma_{k'=1}^{K} \frac{C_{k'}}{(C_{k'}^2 \sigma_v^2 + \sigma_s^2)}}$$

when neither detector noise nor fluctuation noise dominates.

6. A method as in claim 1, wherein the spectroscopic instrument is a tunable diode laser absorption spectroscopy (TDLAS) system.

7. A method of processing tunable diode laser absorption spectroscopy (TDLAS) signals to improve measurement precision, the method comprising:

performing, using a TDLAS instrument, a series of laser scans through a sample gas and measuring a transmission amplitude for each laser scan output as a series of raw intensity measurement data points;

modeling, by a digital signal processor, noise in the raw intensity measurement data points to select weighting coefficients for each laser scan, wherein the selected weighting coefficients are given as $$\widehat{w_k} = \frac{C_k}{\Sigma_{k'=1}^{K} C_{k'}^2}$$

in the case where the noise is dominated by electronic sources independent of measured volume, wherein the selected weighting coefficients are given as $$\widehat{w_k} = \frac{1}{KC_K}$$

in the case where the noise is dominated by changes in measurement volume, and wherein the selected weighting coefficients are given as $$\widehat{w_k} = \frac{C_k}{(C_k^2 \sigma_v^2 + \sigma_s^2)\Sigma_{k'=1}^{K} \frac{C_{k'}}{(C_{k'}^2 \sigma_v^2 + \sigma_s^2)}}$$

in the general case where neither electronic noise nor measurement volume fluctuations dominate the noise, wherein, in each of the above equations, $\widehat{w_k}$ is the selected weighting coefficient, $C_K$ is the measured transmission amplitude of each laser scan k, $\sigma_e^2$ is variance of electronic noise, and $\sigma_v^2$ is variance of noise within the measurement volume;

performing, by the digital signal processor, a weighted average calculation using the selected weighting coefficients upon the raw intensity measurement data points to output a resulting spectrum from the TDLAS instrument with a reduced noise contribution in the measurement data points; and analyzing the resulting spectrum output from the TDLAS instrument to produce a desired measured quantity for the sample gas.

8. The method as in claim 7, wherein the noise to be reduced is caused by electrical sources.

9. The method as in claim 7, wherein the noise to be reduced is caused by process flow variations.

10. The method as in claim 9, wherein the noise to be reduced is caused by attenuation due to dust or particulate.

11. The method as in claim 9, wherein the noise to be reduced is caused by density gradients in the process flow.

12. The method as in claim 9, wherein the noise to be reduced is caused by time-varying transmission losses.

13. The method as in claim 7, wherein the transmission amplitude for each laser scan is determined by peak-to-peak signal amplitude.

14. The method as in claim 7, wherein the transmission amplitude for each laser scan is determined by signal amplitude at a specific measurement point or during a specific duration of time during a TDLAS trace.

15. The method as in claim 14, wherein the transmission amplitude for each laser scan is determined by signal amplitude with a background signal subtracted.

16. The method as in claim 7, wherein the transmission amplitude for each laser scan is determined by a slope of a ramp portion of a TDLAS trace.

17. The method as in claim 7, wherein the selected weighting coefficients are further adjusted for each laser scan based upon similarity to one or more time-adjacent measurement traces either prior or post to a current measurement trace, the adjustment comprising:
- calculating differences between the current measurement trace and a time-adjacent measurement trace;
- squaring the differences;
- calculating an additional weighting factor by summing the squares and taking the inverse of the sum; and
- multiplying this additional weighting factor by the selected weighting coefficients to obtain adjusted weighting coefficients to be applied in the weighted average calculation.

* * * * *